US005693819A

United States Patent [19]
Scharbert

[11] Patent Number: 5,693,819
[45] Date of Patent: Dec. 2, 1997

[54] PROCESS FOR THE SELECTIVE MONO-ORTHO-HYDROXYALKYLATION OF 4-SUBSTITUTED PYRIDINE DERIVATIVES

[75] Inventor: Bernd Scharbert, Frankfurt am Main, Germany

[73] Assignee: Hoechst Atkiengesellschaft, Frankfurt am Main, Germany

[21] Appl. No.: 173,479

[22] Filed: Dec. 27, 1993

Related U.S. Application Data

[63] Continuation of Ser. No. 945,943, Sep. 17, 1992, abandoned.

[30] Foreign Application Priority Data

Sep. 19, 1991 [DE] Germany .................... 41 31 217.1

[51] Int. Cl.$^6$ .................... C07D 213/84; C07D 213/803
[52] U.S. Cl. .................... 546/286; 546/294; 546/312; 546/326; 546/327; 546/323
[58] Field of Search .................... 546/286, 299, 546/312, 326, 327, 323

[56] References Cited

PUBLICATIONS

"Radiation–induced Alkylation, Hydroxyalkylation", and Reduction of Pyridinecarboxamides in Acidic Alcoholic Solutions, Sugimori et al., Bull. Chem. Society of Japan, 55:3055–3056 (1982).
"Nucleophilic Character of Alkyl Radicals V, Selective Homolytic α–Oxyalkylation of Heteroaromatic Bases", Buratti et al., Tetrahedron 27:3655–3668 (1971).
"An Improved Method For The Mono–Hydroxymethylation Of Pyridines, A Modification Of The Minisci Procedure", Katz et al., Synthetic Communications, 19:317–325 (1989).
Citteno et al. Tetrahedron, vol. 41, No. 3, 1985, pp. 617–620.

Primary Examiner—Zinna Northington-Davis
Attorney, Agent, or Firm—Finnegan, Henderson, Farabow, Garrett & Dunner, L.L.P.

[57] ABSTRACT

A process is described for the selective mono-ortho-hydroxyalkylation of 4-substituted pyridine derivatives. In this case a nucleophilic hydroxyalkylation is carried out on the protonated pyridine derivative under the action of peroxodisulfate.

9 Claims, No Drawings

PROCESS FOR THE SELECTIVE MONO-ORTHO-HYDROXYALKYLATION OF 4-SUBSTITUTED PYRIDINE DERIVATIVES

This application is a continuation of Ser. No. 07/945,943 filed Sep. 17, 1992, now abandoned.

The invention relates to a process for the selective mono-ortho-hydroxyalkylation of 4-substituted pyridine derivatives, in which a nucleophilic hydroxyalkylation is carried out on the protonated pyridine derivative under the action of peroxodisulfate.

2-Hydroxymethyl-pyridine derivatives which carry —$CO_2CH_3$ and —$CONH_2$ groups in the 4 position are known in the literature. Likewise, processes are described in which, starting from the corresponding isonicotinic acid derivatives, the derivatives mentioned can be prepared in low yield by UV irradiation at 254 nm (6% yield (—$CO_2CH_3$); 42% yield (—$CONH_2$); Bull. Chem. Soc. Jpn. 55 (1982) 3055). The work-up of the crude product is carried out in this case with the use of either preparative HPLC or TLC, both of which procedures are not considered as processes which can be used industrially.

The substitution of nucleophilic radicals on protonated heteroaromatic compounds is known as the MINISCI reaction [Synthesis 1973, 12]. Nucleophilichydroxymethyl radicals can be produced from methanol and peroxodisulfate [Tetrahedron 27 (1971) 3655]. They attack protonated hetero-aromatic compounds preferentially in the 2-, 4- and 6-positions. For pyridine derivatives substituted in the 4-position with CN, Cl, $CH_2N(CH_3)_2$, it is reported that the use of Minisci conditions only gives yields of 20–30% [Synth. Commun. 19 (1989) 317]. The authors state that the similar reactivity of the starting compound and of the singly hydroxymethylated product means that doubly hydroxymethylated compounds as unwanted by-products greatly restrict the practical applicability of the Minisci reaction, if more than one free position in the 2-, 4- and 6-positions is accessible. They therefore oxidize the pyridine compound to give the corresponding N-oxide, methylate this at the N-O function and only then apply the Minisci reaction to the N-methoxypyridinium compound. By this route they obtain a 71% (4-position: Cl) or 40% (4-position: CN) yield of desired compound relative to the N-oxide.

However, the processes described for single hydroxymethylation with simultaneous suppression of double hydroxymethylation only deliver low yields. When chlorine appears in the 4-position, the yield is better. However, a three-stage synthesis must be performed, which can only be realized industrially with considerable effort.

It was therefore the object of the present invention to provide a process for the preparation of mono-ortho-hydroxyalkylated 4-substituted pyridine derivatives which can be carried out industrially in a simple manner and produces the desired product in good yields.

The object is achieved by a process in which a 4-substituted pyridine derivative of the formula I

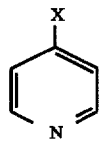

(I)

in which

X is $COOR^1$, $CONH_2$, $CONHR^1$, $CON(R^1)_2$, CN, C(O)$R^1$, $SO_2R^1$, $SO_3H$ or $NO_2$, in which $R^1$ is hydrogen, ($C_1$–$C_{12}$)-alkyl, in particular ($C_1$–$C_6$)-alkyl, or ($C_6$–$C_{12}$)-aryl, in particular phenyl, is converted into a compound of the formula II

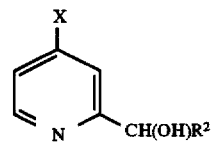

(II)

in which $R^2$ is H or ($C_1$–$C_6$)-alkyl, preferably H, which comprises taking the compound according to formula I in methanol at a concentration of 0.01 to 1 mol/l and adding a 0.01 to 1 molar amount of sulfuric acid and then 0.01 to 4 mol/l of an aqueous solution of an alkali metal peroxodisulfate or ammonium peroxodisulfate.

Preference is given to a compound of the formula I, in which X is $COOR^1$, $CONH_2$, $CONHR^1$, $CON(R^1)_2$ or $C(O)R^1$.

Preference is likewise given to processes in which the compounds are reacted at a concentration of 0.05 to 0.2 mol/l with 0.05 to 0.1 mol/l of sulfuric acid and 2 to 3 mol/l of peroxodisulfate.

After addition of the sulfuric acid, the mixture is preferably brought to a temperature between 50° and 150° C., in particular to the boiling temperature of the alcohol.

The peroxodisulfate to be subsequently added is preferably introduced to the reaction at the abovementioned temperature. After the addition of peroxodisulfate is completed, the reaction is preferably continued for up to 2 h, preferably up to 0.2 h. In view of the reaction time of 24 h conventionally maintained in Minisci reactions, this is seen as an essential advantage of the process according to the invention.

The quantity of peroxodisulfate used in relation to the pyridine compound used according to the invention is between 1 and 4 times the molar amount, preferably between 1.3 and 1.8 times.

After cooling, the mixture is neutralized and extracted with an organic solvent, preferably ethyl acetate. Product and starting compound in the organic extracts can be separated from each other by distillation, recrystallization or sublimation; a double thin-layer evaporation is preferably carried out.

The conversion is dependent on the amount of peroxodisulfate used. If a 1.3–1.8 times a molar amount of peroxodisulfate is used, relative to the compound of the formula I, the ortho-hydroxymethylated pyridine derivative is obtained in a yield of approximately 70%, at a conversion of approximately 70%. The formation of the by-product doubly hydroxymethylated in the ortho position is in this case surprisingly highly repressed. If the molar quantity used of peroxodisulfate is chosen too small, the conversion is too low, as shown in Example 3. For X=$CO_2CH_3$ and a 1.25-fold molar quantity used of peroxodisulfate, the conversion of the compound of the formula I is only just 25 molar %.

If the molar quantity used of peroxodisulfate is too high, more product of the formula II is indeed formed, relative to the starting amount, but too much doubly hydroxymethylated by-product is also formed, so that the yield relative to conversion is greatly reduced (cf. Example 4).

The product prepared by the process according to the invention can be separated from the compound of formula I by distillation.

If the conversion is kept so low that hardly any doubly hydroxymethylated compounds are formed, the product can also be separated from the compound of formula I by placing the reaction mixture into a solvent in which the starting compound is soluble but in which the product is not. Such a solvent can contain as components cyclohexane, aliphatic ethers such as dimethyl ether, diisopropyl ether or methyl tert-butyl ether, halogenated hydrocarbons having at least two carbon atoms, such as dichloroethane, trichloroethylene or tetrachloroethylene, or aromatic compounds such as benzene or toluene.

Solvent mixtures of these components are likewise possible. Particular preference is given to cyclohexane and/or mixtures in which cyclohexane in particular makes up the predominant amount.

The product can then be further purified by recrystallization. The starting compound can be returned to the reaction.

Contrary to the expectations derived from the prior art, the reaction can proceed, instead of with stoichiometric amounts of sulfuric acid, alternatively with catalytic amounts of sulfuric acid. The advantage is, inter alia, that acid-labile substituents such as —$CO_2R^1$ are not hydrolyzed to give —$CO_2H$ during the reaction. Finally, during the work-up, less salt is produced in the neutralization.

The compounds of formula II prepared by the process according to the invention are, according to German Patent Nos. 4131219.8 and 4136346.9 used as inhibitors for proline hydroxylase and lysine hydroxylase for selective inhibition of the biosynthesis of collagen by influencing the collagen-specific hydroxylation reactions.

In addition, the compounds of the formula II where $R^2=H$, which can be prepared by the process according to the invention, can easily be oxidized to give compounds of the formula III.

(III)

If X=$CO_2R^1$ and if an alkaline solution is employed, the pyridine-2,4-dicarboxylic acid is obtained directly, for example by an electrochemical oxidation at NiO (OH) anodes. This process is disclosed in U.S. patent application Ser. No. 07/946,190, filed Sep. 17, 1992, now U.S. Pat. No. 5,259,933.

According to DE-A-3,432,094, these compounds can also be used for the inhibition of proline hydroxylase and lysine hydroxylase.

The invention is described in more detail by the following examples.

EXAMPLE 1

Synthesis of 2-hydroxymethyl-4-carboxymethylpyridine at a molar ratio of peroxodisulfate to starting compound of 1.76.

155 g (1.15 mol) of methyl isonicotinate are dissolved in 1.5 l of methanol, 5 ml of concentrated sulfuric acid are added and the mixture is heated to reflux. In the course of 20 minutes, a saturated, aqueous solution of 460 g (2.02 mol) of ammonium peroxodisulfate is added dropwise to this solution and the mixture is stirred for 10 min at reflux temperature. After cooling, the mixture is filtered, the methanol is removed from the filtrate by distillation, the remaining solution is neutralized using sodium carbonate and is extracted with ethyl acetate. 169 g of a yellow liquid residue remain in the organic phase, which residue contains the following components in % by weight according to GC: methyl isonicotinate 37%, 2-hydroxymethyl-4-carboxymethylpyridine 45%, 2,6-bis(hydroxymethyl)-4-carboxymethylpyridine 5%.

The residue is heated to 60° C. and is subjected to a thin-layer evaporation at 100° C. bath temperature and 0.2 mbar. 59 g of starting compound distill over. A second thin-layer evaporation at 160° C. bath temperature and 0.2 mbar gives 75 g of a solid residue which gives 72 g of product after washing with cyclohexane. A further 4 g of starting compound are obtained from the washing solution after evaporation.

The consumption of methyl isonicotinate is 92 g (0.67 mol), the yield of 2-hydroxymethyl-4-carboxymethylpyridine is 72 g (0.43 mol), corresponding to 64% of theory.

EXAMPLE 2

As Example 1, except using a different work-up.

Purification by distillation is not used. The yellow liquid residue is stirred with cyclohexane to precipitation and filtered off using suction. A solid then remains which, after washing with cyclohexane, yields 71 g of 2-hydroxymethyl-4-carboxymethylpyridine. The cyclohexane used in the stirring and an oily liquid, which form a two-phase system, remain in the filtrate. The cyclohexane phase is separated off and is concentrated together with the washing solution. 35 g of starting compound remain. The consumption of methyl isonicotinate is 120 g (0.88 mol); the yield of 2-hydroxymethyl-4-carboxymethylpyridine is 71 g (0.43 mol), corresponding to 49% of theory.

EXAMPLE 3

As Example 1, except that a molar ratio of peroxodisulfate to starting compound of 3.5 is used.

7.88 g (0.056 mol) of methyl isonicotinate are dissolved in 75 ml of methanol, 0.5 ml of concentrated sulfuric acid is added and the mixture is heated to reflux. In the course of 20 minutes, a saturated, aqueous solution of 45.0 g (0.2 mol) of ammonium peroxodisulfate is added dropwise to this solution and the mixture is stirred for 1 h at reflux temperature. After cooling, the mixture is filtered, the methanol is removed from the filtrate by distillation, the remaining solution is neutralized using sodium carbonate and is extracted with ethyl acetate. 7.1 g of a yellow liquid residue remain in the organic phase, which residue contains the following components in % by weight according to GC: methyl isonicotinate 10%, 2-hydroxymethyl-4-carboxymethylpyridine 58%, 2,6-bis-(hydroxymethyl)-4-carboxymethylpyridine 24%.

EXAMPLE 4

As Example 1, except that a molar ratio of peroxodisulfate to starting compound of 1.25 is used.

7.88 g (0.056 mol) of methyl isonicotinate are dissolved in 75 ml of methanol, 0.5 ml of concentrated sulfuric acid are added and the mixture is heated to reflux. In the course of 20 minutes, a saturated, aqueous solution of 16.0 g (0.07 mol) of ammonium peroxodisulfate is added dropwise to this solution and the mixture is stirred for 1 h at reflux temperature. After cooling, the mixture is filtered, the methanol is removed from the filtrate by distillation, the remaining solution is neutralized using sodium carbonate and is extracted with ethyl acetate. 7.2 g of a yellow liquid residue remain in the organic phase, which residue contains the following components in % by weight according to GC: methyl isonicotinate 63%, 2-hydroxymethyl-4-carboxymethylpyridine 27%, 2,6-bis-(hydroxymethyl)-4-carboxymethylpyridine less than 1%.

EXAMPLE 5

Synthesis of 2-hydroxymethyl-4-cyanopyridine at a molar ratio of peroxodisulfate to starting compound of 1.6.

5.2 g (0.05 mol) of 4-cyanopyridine are dissolved in 75 ml of methanol, 0.5 ml of concentrated sulfuric acid are added and the mixture is heated to reflux. In the course of 20 minutes, a saturated, aqueous solution of 18.2 g (0.08 mol) of ammonium peroxodisulfate is added dropwise to this solution and the mixture is stirred for 1 h at reflux temperature. After cooling, the mixture is filtered, the methanol is removed from the filtrate by distillation, the remaining solution is neutralized using sodium carbonate and is extracted with ethyl acetate. 5.6 g of a solid residue remain in the organic phase, which residue contains the following components in % by weight according to GC: 4-cyanopyridine 27%, 2-hydroxymethyl-4-cyanopyridine 53%, 2,6-bis(hydroxymethyl)-4-cyanopyridine-7%.

I claim:

1. A process for the preparation of a pyridine derivative mono-hydroxyalkylated in the ortho position according to the formula II

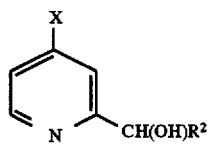
(II)

in which $R^2$ is H, which comprises reacting a compound according to the formula I

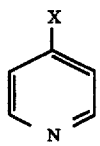
(I)

in which

X is $COOR^1$, $CONH_2$, $CONHR^1$, $CON(R^1)_2$, CN, C(O) $R^1$, $SO_2R^1$, $SO_3H$ or $NO_2$, in which, $R^1$ is hydrogen, $(C_1-C_{12})$-alkyl or $(C_6-C_{12})$-aryl, in methanol at a concentration of 0.01 to 1 mol/l, with 0.1 to 4 mol/l of an aqueous solution of an alkali metal peroxodisulfate or ammonium peroxodisulfate, and a catalytic amount of sulfuric acid, wherein the amount of peroxodisulfate, relative to the pyridine derivative of formula II, is 1 to 4 times the molar amount.

2. The process as claimed in claim 1, wherein the compound according to formula I is present at a concentration of 0.05 to 0.2 mol/l.

3. The process as claimed in claim 1, wherein the compound according to formula I is reacted with 2 to 3 mol/l of the aqueous solution of an alkali metal peroxodisulfate or ammonium peroxodisulfate.

4. The process as claimed in claim 1, wherein the catalytic amount of sulfuric acid is added in an amount of 0.05 to 0.1 mol/l.

5. The process as claimed in claim 1, wherein, after addition of the sulfuric acid, the temperature is brought to 50° to 150° C.

6. The process as claimed in claim 1, wherein, after the addition of peroxodisulfate is completed, the reaction is continued for up to 2 hours.

7. The process as claimed in claim 1, wherein the amount of peroxodisulfate, relative to the pyridine derivative of formula II, is 1.3 to 1.8 times the molar amount.

8. The process as claimed in claim 5, wherein the temperature is brought up to the boiling temperature of the methanol.

9. The process as claimed in claim 6, wherein the reaction is continued for up to 0.2 hour.

* * * * *

UNITED STATES PATENT AND TRADEMARK OFFICE
CERTIFICATE OF CORRECTION

PATENT NO. : 5,693,819
DATED : December 2, 1997
INVENTOR(S) : Bernd SCHARBERT

It is certified that error appears in the above-indentified patent and that said Letters Patent is hereby corrected as shown below:

Claim 1, column 6, line 2, "C(O)" and line 3, "R$^1$," should be on the same line and should read --C(O)R$^1$--.

Signed and Sealed this

Nineteenth Day of May, 1998

Attest:

BRUCE LEHMAN

Attesting Officer

Commissioner of Patents and Trademarks